United States Patent [19]

Clarke, Jr.

[11] Patent Number: 4,917,837

[45] Date of Patent: Apr. 17, 1990

[54] GYPSUM-BASED INSECTICIDE PELLETS AND METHOD OF MANUFACTURE

[76] Inventor: John L. Clarke, Jr., 402 Fairbank Rd., Riverside, Ill. 60546

[21] Appl. No.: 125,150

[22] Filed: Nov. 25, 1987

Related U.S. Application Data

[63] Continuation-in-part of Ser. No. 904,905, Sep. 8, 1986, abandoned.

[51] Int. Cl.⁴ ............................................... B29B 9/08
[52] U.S. Cl. ...................................... 264/37; 264/109; 264/118; 264/122; 264/333
[58] Field of Search ................... 264/117, 37, 109, 118, 264/333, 122

[56] References Cited

U.S. PATENT DOCUMENTS

| | | | |
|---|---|---|---|
| 3,953,378 | 4/1976 | Lasser | 252/522 |
| 4,163,674 | 8/1979 | Been | 106/109 X |
| 4,264,543 | 4/1981 | Valenta | 264/37 |
| 4,670,039 | 6/1987 | Sjogren | 71/34 |
| 4,732,762 | 3/1988 | Sjogren | 424/409 |

FOREIGN PATENT DOCUMENTS

| | | |
|---|---|---|
| 702663 | 1/1965 | Canada . |
| 816050 | 6/1969 | Canada . |
| 1129668 | 8/1982 | Canada . |

*Primary Examiner*—Jan H. Silbaugh
*Assistant Examiner*—Mary Lynn Fertig
*Attorney, Agent, or Firm*—Kinzer, Plyer, Dorn, McEachran, Jambor

[57] ABSTRACT

A gypsum-based pesticide product and method of manufacture of such product in which the product has a release time for the pesticide which is determined at least in part by its size and in which the gypsum is a solid formed by the bonding of plaster of Paris and water. The product, prior to formation of the solid, includes, by weight, no more than about 20% water, approximately 5% of pesticide, with the balance being plaster of Paris. The ingredients, prior to formation into a solid, are intimately mixed for a time period which is only a fraction of the setting time of the mixture with the amount of water being no greater than that required to completely set the plaster of Paris into gypsum.

11 Claims, No Drawings

GYPSUM-BASED INSECTICIDE PELLETS AND METHOD OF MANUFACTURE

SUMMARY OF THE INVENTION

This is a continuation-in-part of copending application Ser. No. 904,905, filed Sept. 8, 1986, now abandoned.

The present invention relates to a gypsum-based pesticide product and a method of manufacturing such product and is particularly concerned with such a product and method in which the amount of water used in the manufacturing process, and therefore present in the finished product, is no greater than the minimum amount required to completely set plaster of Paris into gypsum.

Another purpose is a method of manufacturing a gypsum-based pesticide product in which the time required to mix the pesticide, water and plaster of Paris is only a fraction of the setting time of the mixture, thereby permitting the mixture to be subsequently formed into pellets or briquets of various sizes and shapes.

Another purpose is a method of the type described in which plaster of Paris, water and a pesticide, with the water amount being no greater than the minimum amount required to completely set the plaster of Paris into gypsum, is intimately mixed by a rotating mixing means within a chamber and in which the mixing time is no greater than about five seconds.

Another purpose is a method of manufacturing a gypsum-based pesticide useful in destroying mosquito larvae in which different pesticides may be used and in which the product may be manufactured in a variety of sizes.

Another purpose is a product of the type described which has a long release time and which is of a size to efficiently seed a mosquito breeding area, for example by helicopter.

Another purpose is a method of manufacturing a gypsum-based pesticide as described in which, because of the short time required for mixing, there is the opportunity for substantial recycling of unusable and unset screenings.

Other purposes will appear in the ensuing specification and claims.

DESCRIPTION OF THE PREFERRED EMBODIMENT

The present invention relates to a gypsum-based pesticide and in particular to such a product which is useful in destroying mosquito larvae. Although the invention will be described in connection with pesticides particularly known for killing mosquito larvae, the product may, with the use of different pesticides or herbicides, be useful in destroying other types of pests and both terrestrial and aquatic weeds. The invention may also be useful as a carrier for insect repellents.

Considering the application to destroy mosquito larvae, the eggs which will ultimately become mosquitos are normally laid on dry land adjacent a wet or marshy area. The eggs do not become mosquito larvae until they are in water and may in fact remain in the egg state for as long as eight years if the eggs are not hatched by being covered with water. Once water reaches the eggs, there is a period of approximately 5–15 days during which the mosquito larvae will be transformed through several stages until ultimately becoming mosquitos.

The time to destroy mosquitos is when they are in the larval stage. For this purpose it has been common to spray or seed an area known to be productive of mosquito larvae with some form of liquid or solid product which will release an insecticide over a period of time. However, because of the relatively short incubation period, 5–15 days, it is not always possible to completely cover a large mosquito breeding area during the time when the larvae are hatching. For this reason, the various municipalities which are concerned with destroying mosquito larvae have long sought a product which is of a size to efficiently seed an area by helicopter and which will have a long release time.

The principal factor in determining the release time of pesticides which are in solid form is the size of the product and the manner in which the pesticide is embodied into its carrier. The larger products, for example briquets of the 50 gram size, of necessity must be placed in a mosquito breeding area by hand. Whereas, smaller products, for example those in the 2 gram category, or 0.1 gram and less, may be applied by helicopter, substantially reducing the time and cost in seeding a mosquito breeding area. However, prior products which were of a size to be distributed by helicopter did not utilize a carrier which would provide a long release time.

For example, in the past the insecticide temephos, known by the trademark ABATE and manufactured by American Cyanamid, was sprayed on sand or clay particles and then this material was spread over a mosquito breeding area. Such products have a life of 24–48 hours, which requires not only more timely application, but subsequent applications, to completely destroy mosquito larvae.

Although briquet-size insecticide products, for example 50 grams, are useful in seeding a mosquito breeding area, the difficulties and expense in distributing such product limit the utility of the product since it must be done by a person walking through an area who carefully places an appropriate amount of such product. It is necessary that the amount of the product which is applied to an area not only be sufficient to destroy the mosquito larvae, but that it also be carefully controlled lest the amount of pesticide be greater than that approved by EPA standards. A far more practical method for distribution of mosquito larvae destroying products is by helicopter or by a power backpack blower or venturi tubes attached to a roots-type blower. In the past it has not been possible to manufacture products of a size which could be distributed by such methods and yet have a release time which would be acceptable.

A practical material for the carrier of an insecticide or pesticide is plaster of Paris which forms a gypsum-type product. The pesticide is intimately bonded with the plaster of Paris and is basically released when water dissolves the solid gypsum, thus slowing release time. Gypsum-based insecticides have been known; for example, the product known as ALTOSID made by Zoecon Corporation of Dallas, Tex., uses the insecticide methoprene. However, the size of this product, approximately six grams, has not made it practical for helicopter or power backpack distribution.

Normal plaster of Paris utilizes a large amount of water to form a slurry. Although such a slurry may be practical to form briquet-size product weighing approximately six grams, trying to pour a plaster of Paris slurry into molds to form small molded pellets would result in a time consuming, labor intensive, impractical molding operation further complicated by a short setting time and excess water in the finished product.

The present invention provides a method of manufacturing a gypsum-based pesticide which permits products as small as 0.1 gram and which provides a means for the intimate mixing of the product ingredients in only a fraction of the time required for the mixture to set. The release time is largely determined by the size of the product. The particular pesticide may vary and two known pesticides which are satisfactory are methoprene and temephos manufactured by Zoecon and American Cyanamid, respectively.

Considering specifically a product using the pesticide methoprene, the pesticide in an amount, by weight, of approximately 4.5-5% is mixed with no greater than 20% water, with the balance being plaster of Paris. More specifically, the methoprene may be included in the mixture in the form of a methoprene premix which consists of carbon and methoprene. The carbon not only functions to some degree as a carrier for the methoprene, but principally functions as a sun block to prevent biodegradation of the methoprene. The composition as described is intimately mixed in a mixing device known as a turbolizer, for example of the type used in the mixing of foundry sands and manufactured by Material Processing Corp. of Elmhurst, Ill. Such a device has a chamber in which the water, pesticide and plaster of Paris are introduced and within the chamber is a series of rotating blades which rotate at an extremely high speed and will intimately mix the described mixture in no more than 3-5 seconds.

The mixture described, after going through the turbolizer, can either go to a pellet mill of the type manufactured by CPM Corporation of San Francisco, Calif., which will provide pellets of approximately 0.1 gram up to 2 grams, or the mixture is supplied to a briquet-making machine which can provide briquets in 6 gram and 22 gram sizes.

Because the mixture leaving the turbolizer has a short setting time and there is the consequent possibility that the material may partially harden during transit time to the pellet mill, it is necesary to air blast the wet powder from the turbolizer into the pellet mill dies. It is preferred to use air pressure in the range of 40-60 psi and an air curtain transvector of the type made by Vortec of Cincinnati, Ohio. Movement of the blended wet powder by air, in effect forming an air slide, prevents the wet powder from adherinq to metal surfaces in the pellet mill feed tube and creating a buildup of material which eventually blocks the feed tube entrance.

The mixture described has a short setting time, for example ten minutes, because the amount of water used is the minimum required to completely set the plaster of Paris into gypsum. The amount of water required is 18.6% of the weight of the plaster of Paris and, thus, normally the maximum water used in the process described herein will be no more than 20%. With such an amount of water the setting time is short, but since only a fraction of the setting time has been used in the mixing stage, no more than five seconds, there is adequate time for the mixture to pass through either a pellet mill or a briquet-making machine.

The product coming from either the pellet mill or the briquet making machine, which will have the composition described, will then be applied to a tumbling or vibrating screen in which undersized products are screened out and in which the webbing normally attendant to product formation will be knocked off the pellets or briquets. The pellets are moved from the pellet mill to the screen on a corrugated belt and during such movement, of approximately two minutes' duration, air is drawn over the pellets to cool them with the same cooling air preferably being applied to the pellets as they are screened. In this way, pellet temperatures are dropped from 165° F. to 110° F. in approximately three minutes. This prevents heat degradation of the incorporated insecticides. The screening step thus not only sizes the product, but permits the product to cool and to reduce the free moisture unnecessary for bonding.

Any fines from the screening process may be sent back to the mixing chamber for recycling. A large mesh screen is essential at the oversize/undersize outlet to the recycling return because accumulated residue which breaks off from the sizing screens may be sufficiently large in size that if passed through the recycling step would subsequently jam the pellet mill with consequent damage to it. However, the important point in terms of the screening process is not only to size the product, but to permit adequate drying and cooling time. Recycling is economically important in making the maximum use of the ingredients and is possible because of the short mixing and forming cycle.

In addition to methoprene-based pesticide pellets or briquets, the pesticide temephos may be similarly used. A mixture consisting of about 5% temephos, no more than 20% water, with the balance plaster of Paris, can also be utilized in the described process. A temephos insecticide as commercially available is in the form of an emulsifiable concentrate. In the case of temephos, it is not necessary to have a sun blocking ingredient in this particuar formulation.

In addition to the products described, which are formed into their final product size and shape by either a pellet mill or a briquet making machine, the turbolizer may be modified by removing some of the rotating blades therein and utilizing fingers, whereby the product resulting from the mixing process will not be a mixture which is then sent on to a pellet mill or other type of product forming machine, but rather is in the form of granules, substantially, but not completely, hardened and having a size no greater than about 0.1 gram. Such products themselves are useful in destroying mosquito larvae and do not require the subsequent forming step, but do require screening. Thus, the turbolizer itself may be the last stage in product formation when it is modified to provide semi-hardened granules at its output.

The use of gypsum as a carrier for a pesticide is particularly advantageous in that it has a pH of 7, meaning that it is neutral and thus, being neither an acid nor a base, will have no chemical effect on the pesticide.

Of particular importance in the invention is the use of no more water than the minimum required to set the mixture. This insures a product which can be economically manufactured in that there is no requirement for a long drying period for the product to reach a solid state and to reach its minimum final dried weight. Since a minimum amount of water very substantially reduces the setting time of plaster of Paris, it is necessary to provide a method of intimately mixing a pesticide, water and plaster of Paris in a very short period of time, preferably only a fraction of the setting time. This is done by the rotating turbolizer described herein. The mixing is complete in a period of time which provides adequate remaining time for final formation of the product.

Whereas the preferred form of the invention has been shown and described herein, it should be realized that there may be many modifications, substitutions and alterations thereto.

The embodiments of the invention in which an exclusive property or privilege is claimed are defined as follows:

1. A method for forming a gypsum-based pesticide pellet of a size and weight to be machine distributable and having a release time for the pesticide which is determined at least in part by the size of the pellet, and which will release a pesticide generally uniformly over the life of the pellet, and in which the gypsum is a solid formed by the bonding of plaster of Paris and water, comprising the steps of:
   (a) thoroughly mixing a pesticide, plaster of Paris and water with the amount of water being no greater than a minimum required to completely set the plaster of Paris into gypsum so that substantially all water is absorbed in the chemical reaction between the plaster of Paris and water and with a mixing time of no greater than about five seconds,
   (b) using high pressure to introduce the mixture into a pellet mill or briquet-making machine which forms the mixture into a pellet having a size and shape to be machine distributable prior to setting of the mixture, and
   (c) screening the pellet for size and drying.

2. The method of claim 1 wherein the pesticide is temephos.

3. The method of claim 1 wherein the amount of water in the mixture is no more than about 20% by weight.

4. The method of claim 1 wherein the pesticide is methoprene and is in an amount approximately 4.5% by weight of the mixture.

5. The method of claim 1 wherein the pesticide is methoprene and is introduced into the mixture as a composition consisting of carbon and methoprene, and with the carbon functioning as a sun block to prevent degradation of the pesticide.

6. The method of claim 1 wherein the mixture includes about 5% of the pesticide temephos, about 20% water and about 75% plaster of Paris, all by weight.

7. The method of claim 1 wherein the pellet has a final weight of on the order of about 0.1 gram.

8. The method of claim 1 wherein the pellet has a final weight of on the order of about 2 grams.

9. The method of claim 1 wherein the pellet has a final weight of on the order of about 6 grams.

10. The method of claim 1 wherein the pellet has a final weight of on the order of about 22 grams.

11. The method of claim 1 wherein the mixture of the pesticide, plaster of Paris and water takes place in a mixing chamber within a rotating mixing means, the method further including a step of recycling product from the screening step back to the mixing chamber.

* * * * *